United States Patent
Dahl et al.

(10) Patent No.: US 10,751,028 B2
(45) Date of Patent: Aug. 25, 2020

(54) COHERENCE-BASED BEAMFORMING FOR IMPROVED MICROBUBBLE DETECTION IN CONTRAST ENHANCED ULTRASOUND

(71) Applicant: The Board of Trustees of the Leland Stanford Junior University, Palo Alto, CA (US)

(72) Inventors: Jeremy Joseph Dahl, Palo Alto, CA (US); Dongwoon Hyun, Sunnyvale, CA (US); Juergen K. Willmann, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 435 days.

(21) Appl. No.: 15/474,994

(22) Filed: Mar. 30, 2017

(65) Prior Publication Data
US 2017/0281129 A1    Oct. 5, 2017

Related U.S. Application Data

(60) Provisional application No. 62/317,122, filed on Apr. 1, 2016.

(51) Int. Cl.
*A61B 8/08*   (2006.01)
*A61B 8/00*   (2006.01)

(52) U.S. Cl.
CPC ............. *A61B 8/481* (2013.01); *A61B 8/085* (2013.01); *A61B 8/0825* (2013.01); *A61B 8/5207* (2013.01); *A61B 8/5223* (2013.01); *A61B 8/4494* (2013.01)

(58) Field of Classification Search
CPC ....... A61B 8/481; A61B 8/5223; A61B 8/085; A61B 8/5207; A61B 8/0825; A61B 8/4494
See application file for complete search history.

(56) References Cited

U.S. PATENT DOCUMENTS

| | | | |
|---|---|---|---|
| 5,540,909 A | 6/1996 | Schutt | |
| 6,951,540 B2 | 10/2005 | Ebbini et al. | |
| 9,237,898 B2 | 1/2016 | Hossack et al. | |
| 9,329,260 B2 | 5/2016 | Couture et al. | |
| 9,532,769 B2 * | 1/2017 | Dayton | A61B 8/481 |
| 2004/0059225 A1 | 3/2004 | Hao et al. | |
| 2008/0281205 A1 * | 11/2008 | Naghavi | A61B 8/12 600/458 |
| 2013/0109971 A1 | 5/2013 | Dahl et al. | |
| 2015/0023881 A1 | 1/2015 | Kim et al. | |
| 2016/0262727 A1 * | 9/2016 | Dayton | A61B 8/4477 |

OTHER PUBLICATIONS

Hyun et al., "Short-Lag Spatial Coherence Imaging on Matrix Arrays, Part I: Beamforming Methods and Simulation Studies", 2014, IEEE Trans. Ultrasonics, Ferroelectrics and Frequency Control v61n7, pp. 1101-1112.

* cited by examiner

*Primary Examiner* — Sanjay Cattungal
(74) *Attorney, Agent, or Firm* — Lumen Patent Firm

(57) ABSTRACT

Ultrasonic imaging is performed by constructing spatial coherence images of a target having microbubbles in it. The basis for this approach is the observation that the spatial coherence of microbubbles differs from the spatial coherence of tissue and the spatial coherence of image noise. Therefore, imaging based on spatial coherence provides a way to suppress noise signals and tissue signals relative to the microbubble signals.

14 Claims, 7 Drawing Sheets

COHERENCE-BASED BEAMFORMING FOR IMPROVED MICROBUBBLE DETECTION IN CONTRAST ENHANCED ULTRASOUND

CROSS REFERENCE TO RELATED APPLICATIONS

This application claims the benefit of U.S. provisional patent application 62/317,122, filed on Apr. 1, 2016, and hereby incorporated by reference in its entirety.

GOVERNMENT SPONSORSHIP

This invention was made with Government support under contract EB013661 awarded by the National Institutes of Health. The Government has certain rights in the invention.

FIELD OF THE INVENTION

This invention relates to ultrasound imaging.

BACKGROUND

Ultrasound imaging has been employed for various medical applications. Methods of improving imaging performance in such cases are of general interest. One method of improving ultrasound imaging is the use of microbubbles as contrast agents. For example, microbubbles can be configured to specifically bind to tumor antigens to aid in cancer detection. However, new problems can arise in connection with the use of microbubbles as contrast agents. In particular, if it is desired to have the microbubbles remain intact during imaging (as opposed to the more conventional approach of bursting the microbubbles when imaging), then it is necessary to have a relatively low incident acoustic intensity, which undesirably tends to reduce image quality. Accordingly, it would be an advance in the art to provide improved acoustic imaging using microbubbles as contrast agents.

SUMMARY

In this work, ultrasonic imaging is performed by constructing spatial coherence images of a target having microbubbles in it, as opposed to the more conventional signal magnitude images. The basis for this approach is our observation that the spatial coherence of microbubbles differs from the spatial coherence of tissue and the spatial coherence of image noise (see FIG. 2). Therefore, imaging based on spatial coherence provides a way to suppress noise signals and tissue signals relative to the microbubble signals.

DETAILED DESCRIPTION

Section A describes general principles relating to embodiments of the invention, and section B is a detailed experimental example.

A) General Principles

Figure 1:
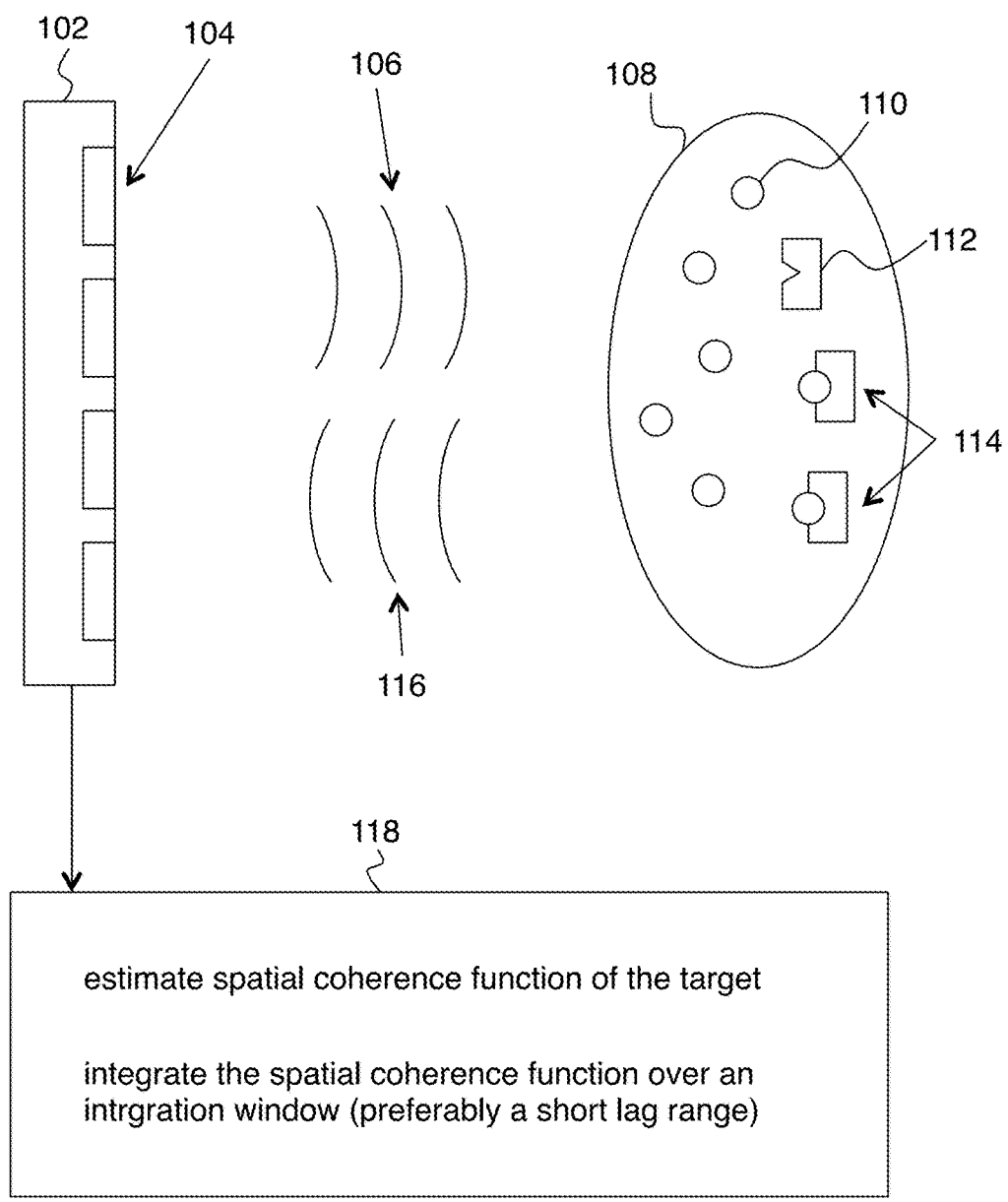
FIG. 1 shows operation of an exemplary embodiment of the invention.

FIG. 1 shows operation of an exemplary embodiment of the invention. An embodiment of the invention is a method for ultrasound medical imaging. The method includes providing a contrast agent 110 to a target being imaged 108, where contrast agent 110 includes microbubbles. Here these microbubbles are schematically shown as small circles within target 108. Incident acoustic radiation 106 is provided to target 108 with an ultrasound transducer array 102. Here this array is shown as having four elements 104, but any number of elements can be included in the transducer array, and the transducer array can be one-dimensional or two-dimensional. Target 108 provides an acoustic signal 116 responsive to the incident acoustic radiation 106. Acoustic signal 116 is received by ultrasound transducer array 102.

Image beamforming to provide an ultrasound image of the target is performed in processor 118. In particular, this beamforming includes at least the following two steps:
i) estimating a spatial coherence function of the target; and
ii) integrating the spatial coherence function over a predetermined integration window. The resulting ultrasound image of the target is a spatial coherence image. Typically the beam forming will also include providing time delays for focusing prior to estimating the spatial coherence function of the target.

The spatial coherence function is a measure of the correlation function between signals with a given spacing, or lag, of m elements. This function is defined at every field point x in the ultrasound image. Thus $Rm(x)$ is the measured correlation coefficient of transducer element signals from field point x for transducer elements having a relative lag of m. For two-dimensional transducer arrays, m refers to a two-dimensional lag, with components in the two dimensions of the array. In some cases, these measured correlation coefficients are computed by averaging over a correlation window (e.g., a one wavelength axial signal window centered at x). In other cases no averaging is needed to provide these correlation coefficients, leading to so-called 'single-pixel' computations. Here field point x can be a pair of two coordinates ($x=(x_1, x_2)$) or a triplet of three coordinates ($x=x_1, x_2, x_3$) for 2D and 3D cases, respectively.

Integration of a spatial coherence function can be performed by analog integration over the appropriate range, but in practice this integration is typically performed by a discrete summation over an appropriate range of indices.

Preferably the microbubbles are configured to have a spatial coherence distinct from a spatial coherence of tissue in the target and distinct from a spatial coherence of measurement noise.

For 1-D transducer arrays, the ultrasound transducer array can have N elements and the predetermined integration window is preferably a lag range from 1 to N/2 and is more preferably a lag range from 1 to N/4. For 2-D transducer arrays, the ultrasound transducer array can have $N_x \times N_y$ elements and the predetermined integration window is preferably a lag range from 1 to $N_x/2$ and from 1 to $N_y/2$ and is more preferably a lag range from 1 to $N_x/4$ and from 1 to $N_y/4$ and is still more preferably the set of all 2-D lags ($m_x$, $m_y$) such that $(1-m_x/N_x)(1-m_y/N_y) > 0.75$. Further details on suitable beamforming methods for short-lag spatial coherence imaging are given in an article by Hyun et al. (IEEE Transactions on Ultrasonics, Ferroelectrics and Frequency Control, v61n7, pp. 1101-1112, 2014) hereby incorporated by reference in its entirety.

In some embodiments, the intensity of the incident acoustic radiation is sufficiently low that the microbubbles do not burst during imaging. In other embodiments imaging is divided into two parts where the first part has an incident acoustic intensity that is sufficiently low that the microbubbles do not burst, and where the second part has an incident acoustic intensity sufficient to burst the microbubbles. Bursting the microbubbles can be used to provide increased acoustic signal and/or to deliver a therapeutic agent.

The incident acoustic radiation is preferably configured as pulse sequences having linear echoes that substantially cancel in the acoustic signal. The microbubbles are preferably configured to provide a nonlinear acoustic signal at one or more frequencies distinct from frequencies in the incident acoustic radiation.

The microbubbles can be configured to specifically bind to features within the target. FIG. 1 shows an example, where microbubbles have bound to features 114 but not to feature 112. Specificity is schematically shown here by feature 112 having a V-shaped slot that does not match the microbubble shape. Specificity for the microbubbles can be provided by any biological molecular pairing mechanism (e.g., antibody-antigen, complementary nucleotides etc.). The target can be any organ or tissue within the body, including but not limited to: heart, liver, kidney, pancreas and breast.

B) Experimental Example

B1) Introduction

Contrast-enhanced ultrasonography (CEUS) utilizes microbubble (MB) contrast agents for enhanced anatomical, functional, and molecular imaging. MB contrast agents have been used effectively in obtaining better images of the heart, liver, kidney, and breast vasculature, and have been used to improve ultrasound imaging in a variety of other applications. MBs typically include a biocompatible shell with a gas core, ranging from 1 to 6 microns in diameter. Despite their small size, MB contrast agents have a strong scattering response to insonification, making them easily detectable with ultrasound. MBs also have a harmonic acoustic signature that is distinct from that of tissue parenchyma. These differences can be leveraged to isolate the MB signal via frequency-based techniques such as harmonic imaging or acoustic angiography.

MBs can also be coated with ligands and antibodies to target specific biomarkers for molecular CEUS (MCEUS) imaging applications. For example, cancerous tissue can be identified by targeting MBs to antigens that are often overexpressed by growing tumors, such as vascular endothelial growth factor receptor 2 (VEGFR2). By combining the sensitivity of ultrasound to MBs and the specificity of MBs to the tumor antigens, MCEUS can be used to aid in the early detection of cancer. Several preliminary studies in preclinical applications have shown the potential for MCEUS.

However, there are numerous challenges towards translating MCEUS to clinical use. MBs are fragile and are easily destroyed by the pressures used in diagnostic ultrasound imaging, and require specially designed low pressure pulse sequences with a low mechanical index (MI), ranging from 0.1 to 0.5. The low pressures required to keep the microbubbles intact result in significantly degraded signal-to-noise ratio (SNR) of the received echoes. This effect is compounded by the presence of subcutaneous tissue layers between the transducer and the tumor, an obstacle that is often ignored in preclinical exams of superficial tumors. The tissue may generate reverberation clutter and phase aberration artifacts, in addition to frequency-dependent attenuation of high frequency echoes.

Much of the current research efforts are centered on developing novel pulse sequences and techniques to improve binding of MBs to receptors. These techniques are used together with the classical delay-and-sum (DAS) beamformer to form images based on the magnitude of the echo. Despite its ubiquity, the DAS beamformer is unsophisticated, and in low SNR imaging environments, is especially subject to imaging artifacts caused by thermal noise and clutter. More sensitive and robust imaging techniques are needed as MCEUS research transitions into clinical applications, where imaging conditions are not ideal.

Short-lag spatial coherence (SLSC) is an alternative beamforming technique that makes images of the spatial coherence of the echo, rather than of its magnitude. The spatial coherence of an echo is a measure of how similar the wavefront is between adjacent elements. In theory, signals from diffuse scatterers such as tissue should be partially coherent, while those from incoherent noises like reverberation clutter should be incoherent. SLSC imaging has demonstrated improved lesion detectability in simulations and in vivo. Higher harmonics of the echoes demonstrate similar trends, and have yielded similar results when used in conjunction with SLSC imaging. These reasons lead us to believe that SLSC is well suited for low SNR in vivo imaging. Furthermore, because beamforming is performed after data acquisition, SLSC can be applied in conjunction with any advances in other aspects of MCEUS, such as pulse sequence techniques.

In this work, we apply SLSC beamforming to MCEUS in a flow channel phantom experiment as well as in a mouse model of hepatocellular carcinoma, comparing the results against those of the conventional DAS beamformer.

B2) Methods

B2a) Beamforming

Conventional CEUS and SLSC-CEUS images were reconstructed using the DAS and SLSC beamformers, respectively. Let $s_i[n]$ correspond to the n-th sample of the focused complex signal from element i, reconstructed by applying the proper focal delays. For an aperture of N elements, the output of the DAS beamformer is computed as:

$$I_{DAS}[n] = |\Sigma_{i=1}^{N} s_i[n]| \qquad (1)$$

The SLSC beamformer includes two steps: estimating the spatial coherence function, and integrating the coherence function at short lags. The spatial coherence function is a measure of the average correlation coefficient between signals with a given spacing, or lag, of m elements. On a 1D array, this can be computed as $$\hat{R}_m[n] = \frac{1}{N-m}\sum_{i=1}^{N-m} r_{i,i+m}[n], \quad (2)$$

where $r_{i,i+m}[n]$ is the correlation coefficient between elements i and i+m:

$$r_{i,i+m}[n] = \frac{\sum_{t\in T} s_i[n+t]s^*_{i+m}[n+t]}{\sqrt{\sum_{t\in T}|s_i[n+t]|^2 \sum_{t\in T}|s_{i+m}[n+t]|^2}}. \quad (3)$$

Historically, the correlation coefficient was computed over a kernel of length T, as in Eq. 3, typically chosen as a one wavelength axial signal window centered at n. Here, we use a kernel-less approach, using a single-sample kernel:

$$r_{i,i+m}[n] = \frac{s_i[n]s^*_{i+m}[n]}{|s_i[n]||s_{i+m}[n+t]|}. \quad (4)$$

The output of the SLSC beamformer is then computed by integrating the spatial coherence function over "short" lags, i.e. for m≤M:

$$I_{SLSC}[n] = \sum_{m=1}^{M} \hat{R}_m[n]. \quad (5)$$

Figure 2:
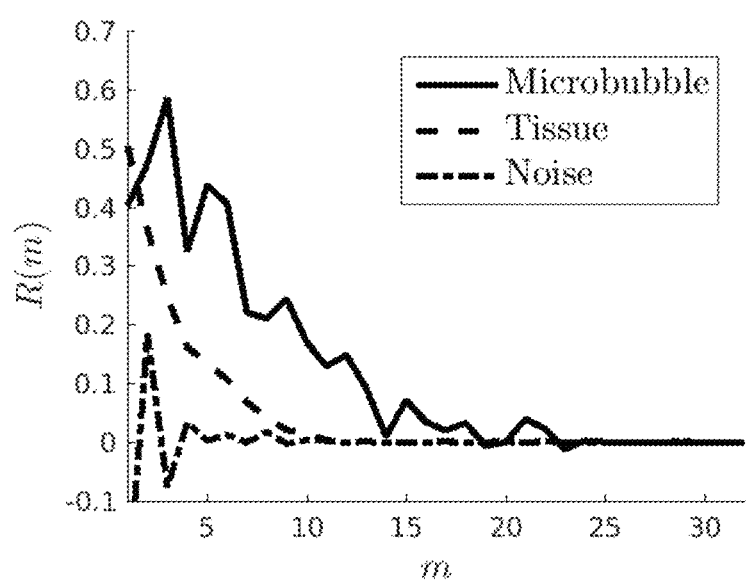
FIG. 2 shows exemplary measured spatial coherence for microbubble, tissue and noise.

The threshold M is usually set to be 25% of the aperture M=N/4. FIG. 2 shows examples of measured spatial coherence functions from MBs, tissue, and incoherent noise. Note that the MBs exhibit a greater level of spatial coherence than tissue or noise, making spatial coherence a good detector of MBs.

B2b) Microbubble Imaging System

A Verasonics (Verasonics, Redmond, Wash.) Vantage 256 research scanner was used to acquire the raw channel data from 128 elements of an L12-3v transducer in real time. The harmonic component of the signal was obtained with a CPS approach, combined with a plane wave synthetic aperture technique. Throughout these experiments, three plane waves were transmitted at each of 7 angles over a span of 18° for a total of 21 pulses per image frame. Each triplet of pulses included a positive, negative, and positive polarity two cycle transmission at 4.5 MHz, where the positive and negative pulses were 180° out of phase. The received echoes were bandpass filtered at the second harmonic frequency (9 MHz) to detect the non-linear MB response. Each triplet of signals was summed together to cancel out the linear component, further emphasizing the harmonic signals.

The data was then transferred to a host computer for processing. Both DAS and SLSC beamformers were implemented as a MATLAB® (Mathworks, Natick, Mass.) MEX function, written in C++ with the CUDA (Compute Unified Device Architecture) application programming interface (API) from NVIDIA (NVIDIA, Santa Clara, Calif.). An NVIDIA Quadro K620 graphics processing unit (GPU) was used to focus, beamform, and display side-by-side conventional CEUS and SLSC-CEUS images in real time at >20 frames per second (fps).

B2c) Experimental Methods

The in vitro experiments were performed in an agarose flow channel phantom. The phantom was made with an agar gel (2% weight-by-volume) mixed with graphite (2%) for tissue-mimicking scattering. The gel was poured into a container lined with ρ-c rubber and with a removable 2 mm diameter plastic tube spanning from wall to wall across the center. The tube was removed after the gel had cooled and set, leaving behind a wall-less flow channel. A solution containing clinical grade BR55 (Bracco, Milan) was injected into the flow channel with a syringe. BR55 is a MB contrast agent targeted to VEGFR2. In this study, BR55 was used as a non-targeted MB because the phantom did not contain any VEGFR2 receptors. Concentrations of $5\times10^4$, $5\times10^5$, $5\times10^6$, and $5\times10^7$ MB/mL were used in this preliminary study. The lowest and highest concentrations were further tested in high-noise environments by reducing the transmit voltage by a factor of 3.

Figure 3:
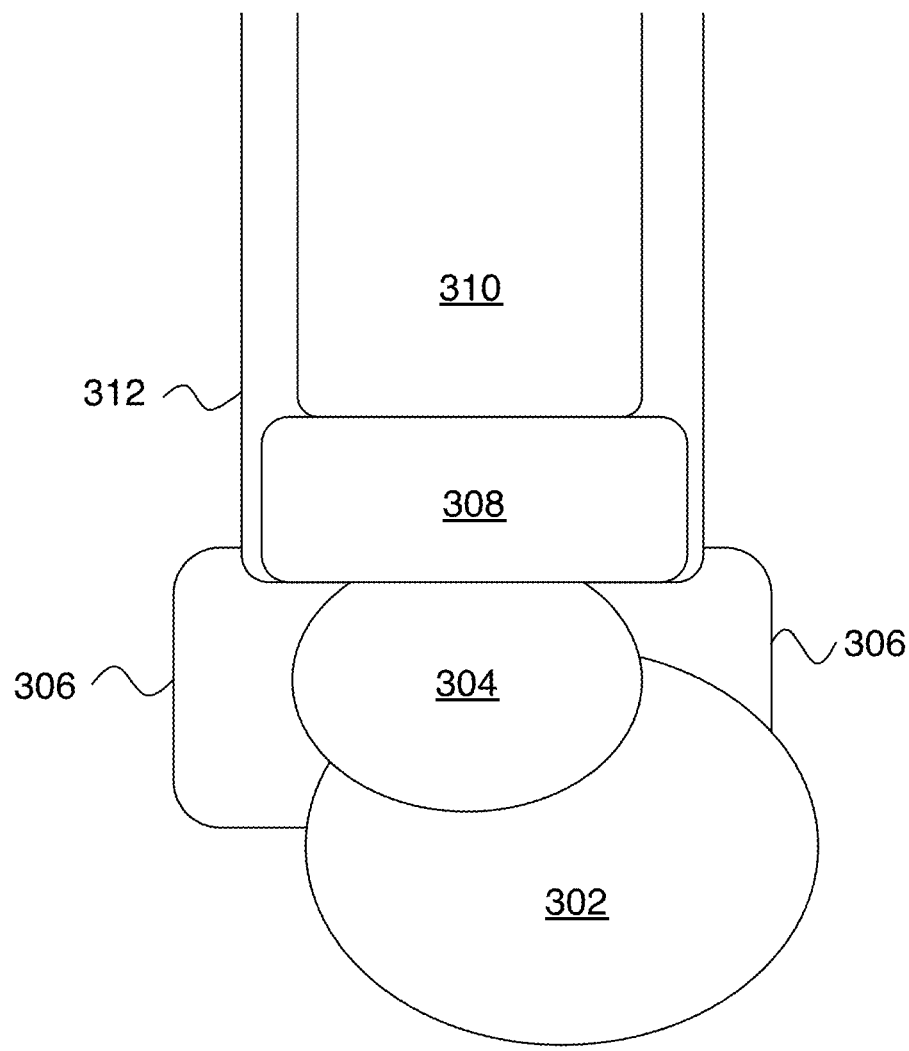
FIG. 3 schematically shows an experimental arrangement for the work of section B below.

In vivo experiments were performed in a mouse model of hepatocellular carcinoma with a xenografted subcutaneous tumor on the hind limb. A 1 cm thick layer of degassed porcine tissue was placed between the transducer and tumor to mimic clinical imaging conditions. FIG. 3 schematically depicts the imaging setup. Here 302 is the mouse, 304 is the tumor, 306 is the gel, 308 is the degassed porcine tissue, 310 is the transducer and 312 is a protective sheath. A total of 10 mice were imaged. The mice were anesthetized with isofluorane prior to imaging. The contrast agent was administered through the tail intravenously at a concentration of $5\times10^7$ MB/mL. The MBs were allowed to circulate through and accumulate in the tumor for 4 minutes post-injection. Images were acquired after the MBs had binded. Control images were also obtained immediately following a high MI destructive pulse, before more circulating MBs could enter the tumor. A difference image was also computed by subtracting the post-burst image from the pre-burst image:

$$I_{diff}[n] = I_{pre}[n] - I_{post}[n]. \quad (6)$$

To enhance the image, multiple frames were averaged together for both $I_{pre}[n]$ and $I_{post}[n]$, with simple motion correction applied using the MATLAB Image Processing Toolbox.

In the experiments, the MB sensitivity of each beamformer was measured as follows:

$$SNR = 20\log_{10}\frac{RMS[I[n_{MB}]]}{RMS[I[n_{Tissue}]]} \quad (7)$$

where RMS is the root-mean-square value, I is either the conventional CEUS or SLSC-CEUS image, and $n_{MB}$ and $n_{Tissue}$ correspond to samples in regions of interest (ROIs) of MB signal and tissue signal, respectively.

B3) Results and Discussion

B3a) Phantom Experiments

The MBs were easily visible in the flow channel phantom for all MB concentrations. The measured SNRs are reported in Table 1. In all cases, the SNR was very high for both conventional CEUS and SLSC-CEUS, indicating that the MBs were easily detected. In each case, SLSC-CEUS had slightly higher SNR, with the greatest disparity at the lowest concentration of MBs tested.

TABLE 1

Imaging SNR in Agarose Phantom

| Concentration | CEUS SNR | SLSC-CEUS SNR |
|---|---|---|
| $5 \times 10^7$ MB/mL | 18.6 dB | 20.9 dB |
| $5 \times 10^6$ MB/mL | 23.9 dB | 24.0 dB |
| $5 \times 10^5$ MB/mL | 19.5 dB | 20.5 dB |
| $5 \times 10^4$ MB/mL | 16.5 dB | 22.0 dB |

In the high-noise imaging environment, a greater difference between the two methods was observed, as shown in Table 2, with SLSC-CEUS outperforming CEUS.

TABLE 2

Imaging SNR in Agarose Phantom in Noisy Conditions

| Concentration | CEUS SNR | SLSC-CEUS SNR |
|---|---|---|
| $5 \times 10^7$ MB/mL | 17.0 dB | 21.4 dB |
| $5 \times 10^4$ MB/mL | 8.5 dB | 15.0 dB |

B3b) In Vivo Experiments

Figure 4A:
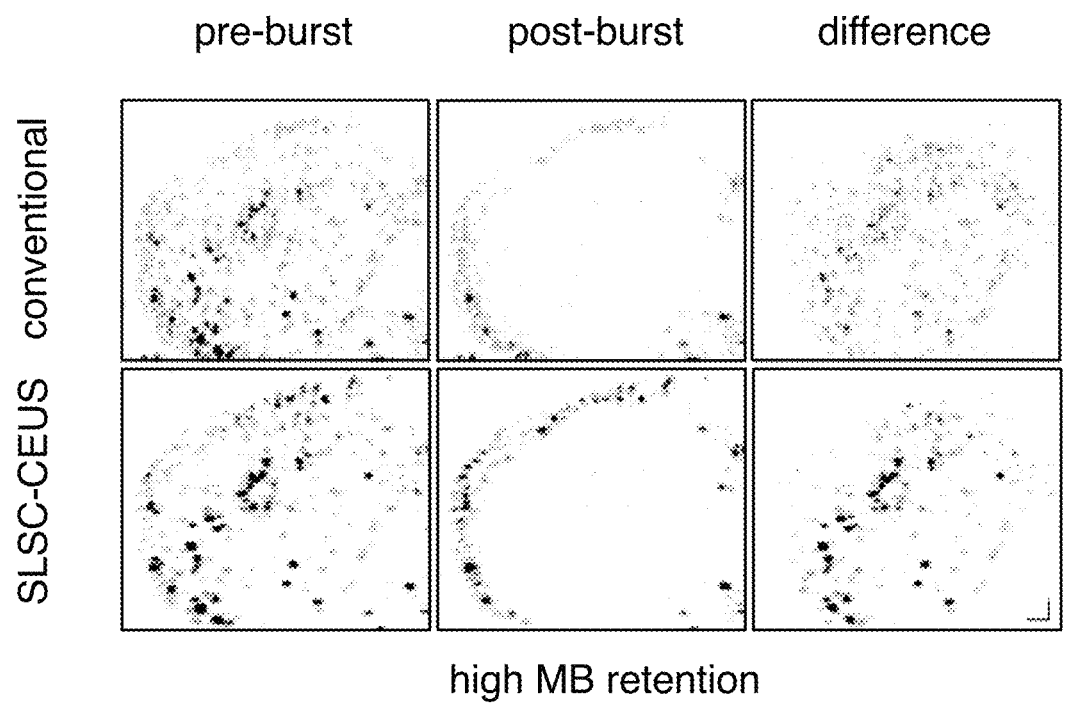
FIG. 4A shows conventional and short-lag spatial coherence (SLSC) images of a tumor having high microbubble retention.
Figure 4B:
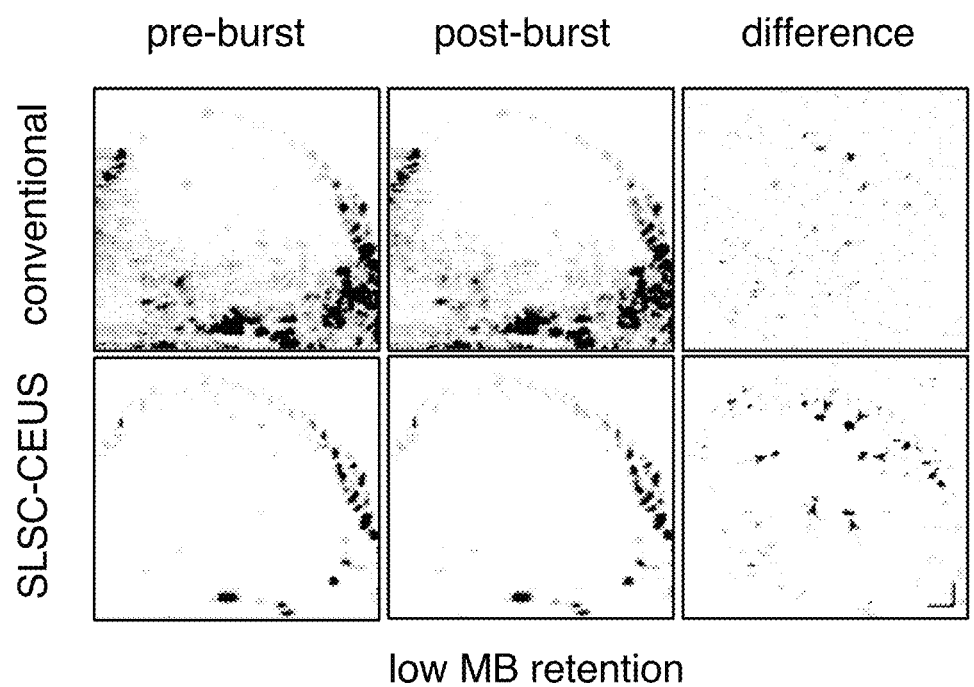
FIG. 4B shows conventional and SLSC images of a tumor having low microbubble retention.

Pre-burst, post-burst, and difference images are shown in FIGS. 4A-B for two tumors. One tumor (FIG. 4A) demonstrated high MB retention while the other (FIG. 4B) had low retention. In both CEUS and SLSC-CEUS images, tissue signal was present in both the pre-burst and post-burst images, but removed in the difference images. The pre- and post-burst images show dynamic ranges of 30 dB for conventional and a normalized linear scale from 0 to 0.9 for SLSC-CEUS. The difference images display 0 to 6 standard deviations in dynamic range. In the high retention case, the SNR of the conventional and SLSC-CEUS techniques was reported to be 4.2 dB and 16.1 dB, respectively. In the low retention case, a quantitative measure could not be performed because the ROIs were too small. The SLSC-CEUS difference image more clearly distinguishes six bound microbubbles (marked with arrows in the lower right part of FIG. 4B) from the background signal.

Figure 5:
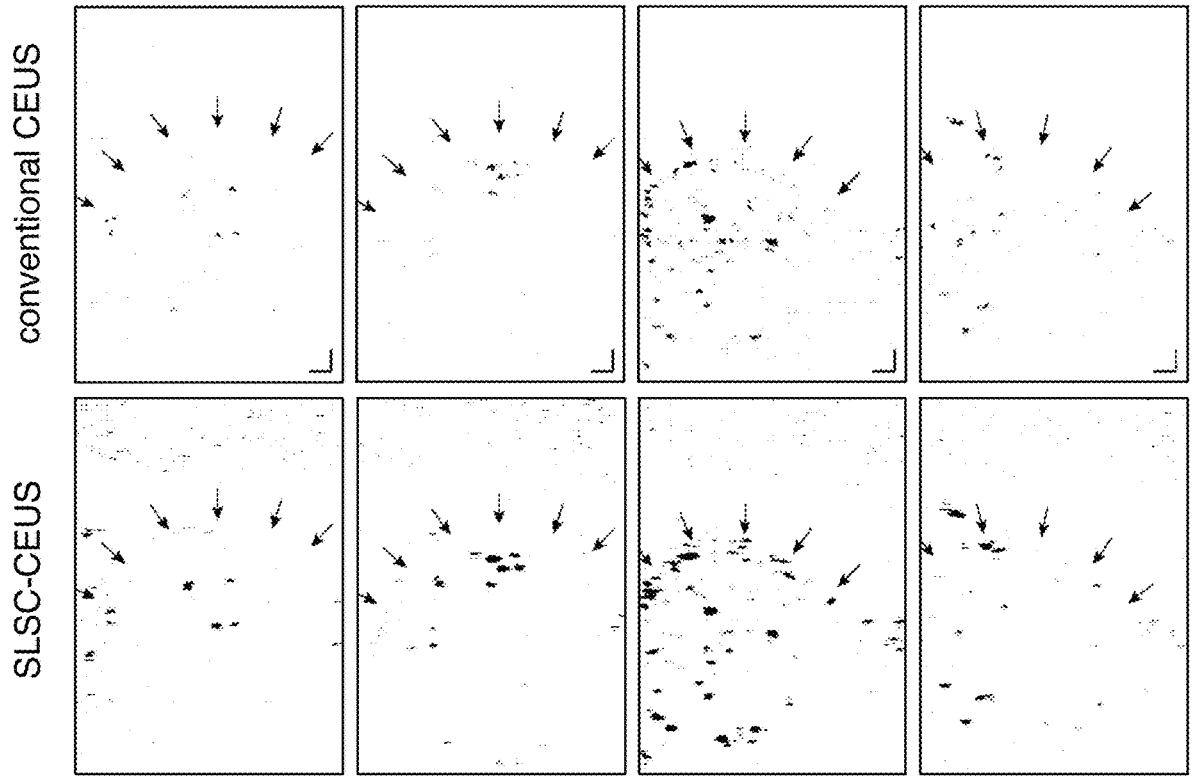
FIG. 5 shows conventional and SLSC images of a tumor having low microbubble retention.

FIG. 5 shows difference images from tumors with low MB retention. The conventional CEUS images are presented in the top row, and SLSC-CEUS in the bottom row. The tumor border is denoted with arrows, and the bars show one millimeter. All images show a dynamic range of 1 to 5 times the RMS of the noise floor, as measured in the porcine tissue in front of the transducer. Qualitatively, the MBs in SLSC-CEUS images were visualized with significantly enhanced clarity while the tissue signal was suppressed. SLSC-CEUS visualized several bubbles deep within the tumor that were not visible in the conventional CEUS images.

Figure 6:
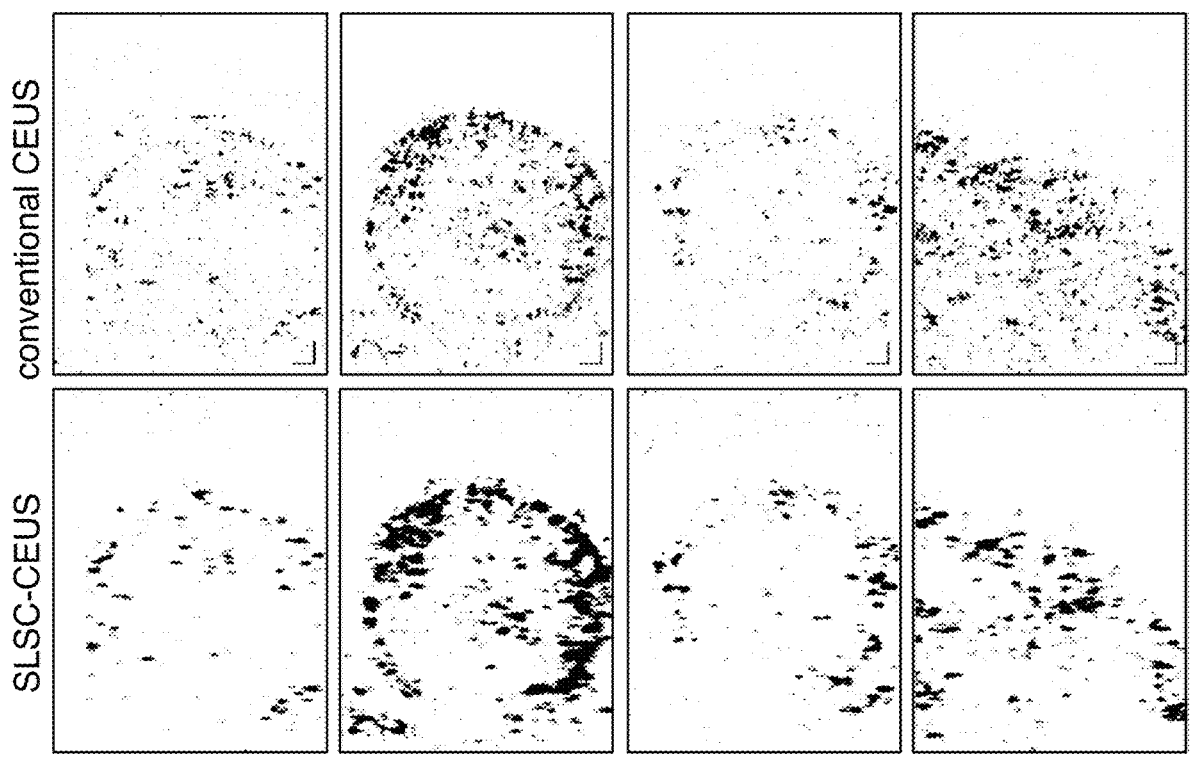
FIG. 6 shows conventional and SLSC images of a tumor having high microbubble retention.

Similarly, FIG. 6 shows difference images from tumors with high MB retention, displayed with the same dynamic range as in FIG. 4. The conventional CEUS images contained a significant level of noise throughout, both inside and outside of the tumor. SLSC-CEUS suppressed signals from outside the tumor and from the tissue while enhancing the MB signal.

Figure 7:
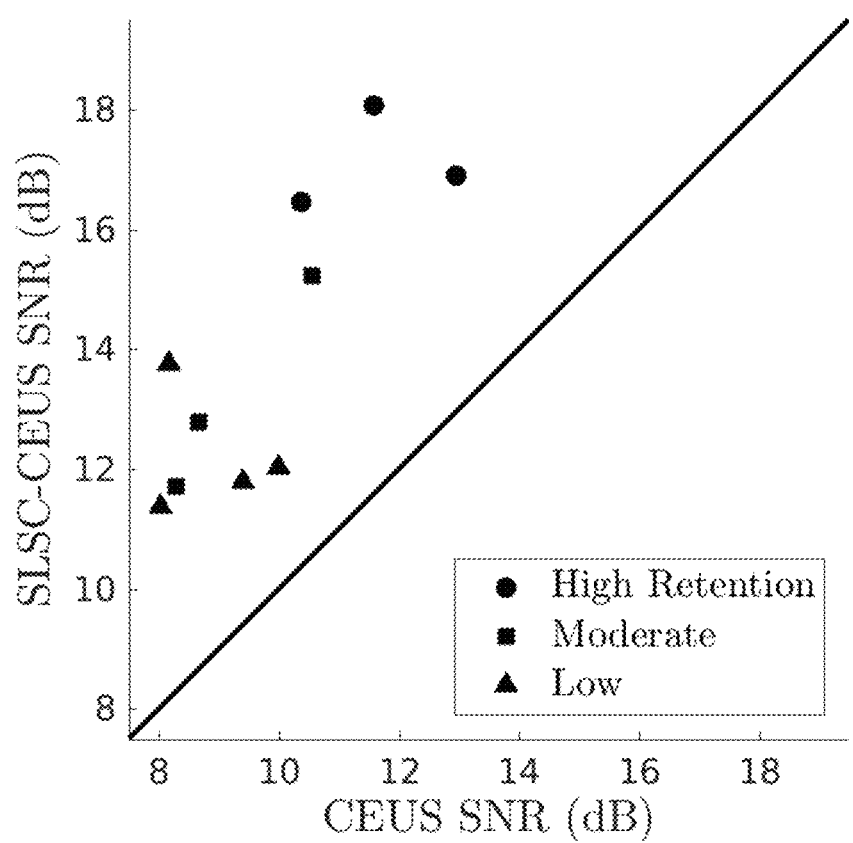
FIG. 7 is a plot showing signal to noise ratio (SNR) for conventional and SLSC imaging for ten imaging studies.

The sensitivities of the SLSC-CEUS images are plotted against those of the conventional CEUS images in FIG. 7 for the 10 imaged mice. In the presence of the porcine layer, SLSC-CEUS improved the SNR in all 10 acquisitions with varying levels of MB retention in the tumor. The average improvement in SNR was 65%, corresponding to 4.3 dB SNR.

B4) Conclusion

In this study, in vivo imaging conditions were mimicked using a layer of porcine tissue. SLSC-CEUS improved the sensitivity in every acquisition, with an average increase of 65% in SNR. The clutter and noise generated in vivo is often spatially incoherent but high in magnitude. The conventional CEUS beamformer, which detects magnitude, interprets the noise as signal. The SLSC beamformer instead detects regions that scatter off echoes with high spatial coherence, regardless of magnitude. This allows SLSC-CEUS to identify echo sources that are weak in magnitude but high in spatial coherence, such as individually bound MBs, and to suppress noise that is high in magnitude and spatially incoherent.

The SLSC beamformer improves sensitivity to targeted MBs in conditions similar to clinical imaging by utilizing the spatial coherence of the echo, and may pave the way for the early detection of cancer in humans.

The invention claimed is:

1. A method for ultrasound medical imaging, the method comprising:
    providing a contrast agent to a target being imaged, wherein the contrast agent includes microbubbles;
    providing incident acoustic radiation to the target with an ultrasound transducer array, wherein the target provides an acoustic signal responsive to the incident acoustic radiation;
    receiving the acoustic signal with the ultrasound transducer array;
    providing an ultrasound image of the target by applying a beamforming method to the acoustic signal;
    wherein the beamforming method includes:
        i) estimating a spatial coherence function of the target;
        ii) integrating the spatial coherence function over a predetermined integration window;
    wherein some or all of the microbubbles are bound to the target;
    wherein the ultrasound image of the target provides improved sensitivity to bound microbubbles relative to noise in the ultrasound image.

2. The method of claim 1, wherein the microbubbles are configured to have a spatial coherence distinct from a spatial coherence of tissue in the target and distinct from a spatial coherence of measurement noise.

3. The method of claim 1, wherein the ultrasound transducer array has N elements and wherein the predetermined integration window is a lag range from 1 to N/2.

4. The method of claim 1, wherein the ultrasound transducer array has $N_x \times N_y$ elements and wherein the predetermined integration window is a lag range from 1 to $N_x/2$ and from 1 to $N_y/2$.

5. The method of claim 1, wherein an intensity of the incident acoustic radiation is sufficiently low that the microbubbles do not burst during imaging.

6. The method of claim 1,
    wherein a first part of an imaging sequence has an intensity of the incident acoustic radiation that is sufficiently low that the microbubbles do not burst during the first part, and
    wherein a second part of the imaging sequence has an intensity of the incident acoustic radiation that is sufficient to burst the microbubbles;
    wherein a difference image between a pre-burst image and a post-burst image is formed to enhance microbubble features in the difference image.

7. The method of claim 1, wherein the incident acoustic radiation is configured as pulse sequences having linear echoes that substantially cancel in the acoustic signal.

8. The method of claim 1, wherein the microbubbles are configured to provide a nonlinear acoustic signal at one or more frequencies distinct from frequencies in the incident acoustic radiation.

9. The method of claim 1, further comprising specifically binding the microbubbles to features within the target.

10. The method of claim 1, wherein the target is selected from the group consisting of: heart, liver, kidney, pancreas, and breast.

11. The method of claim 1, wherein the microbubbles are configured to deliver a therapeutic agent when burst by the incident acoustic radiation.

12. The method of claim 1, wherein the beamforming method includes providing time delays for focusing prior to the estimating a spatial coherence function of the target.

13. The method of claim 1, wherein two or more beams of the incident acoustic radiation are provided to the target, each of the two or more beams having its corresponding acoustic signal, wherein the acoustic signals are combined retrospectively to form a synthetic transmit aperture.

14. The method of claim 1, wherein the improved sensitivity to bound microbubbles relative to noise in the ultrasound image is 3 dB or more.

* * * * *